United States Patent
Brandewie et al.

(10) Patent No.: US 12,171,666 B2
(45) Date of Patent: Dec. 24, 2024

(54) METAL REINFORCED ACETABULAR SHELL LINER

(71) Applicant: DePuy Ireland Unlimited Company, Ringaskiddy (IE)

(72) Inventors: Alena M. Brandewie, Versailles, OH (US); Ryan C. Keefer, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 479 days.

(21) Appl. No.: 16/708,913

(22) Filed: Dec. 10, 2019

(65) Prior Publication Data

US 2021/0169654 A1    Jun. 10, 2021

(51) Int. Cl.
A61F 2/34     (2006.01)
B32B 15/06    (2006.01)
B33Y 80/00    (2015.01)

(52) U.S. Cl.
CPC .............. *A61F 2/34* (2013.01); *B32B 15/06* (2013.01); *A61F 2002/3441* (2013.01);
(Continued)

(58) Field of Classification Search
CPC .............. A61F 2/34; A61F 2002/3441; A61F 2002/345; A61F 2/4684; A61F 2002/30011; A61F 2002/30331; A61F 2002/30332; A61F 2002/30474; A61F 2002/3092; A61F 2002/30971; A61F 2002/30985; A61F 2/30767; B32B 15/06; B32B 2305/026; B32B 2309/105; B32B 2311/00; B32B 2250/03; B32B 1/00; B32B 9/005;
(Continued)

(56) References Cited

U.S. PATENT DOCUMENTS 3,707,006 A    12/1972   Bokros et al.
3,801,989 A     4/1974   McKee
(Continued)

FOREIGN PATENT DOCUMENTS

CN    2244386 Y    1/1997
CN    2580920 Y   10/2003
(Continued)

OTHER PUBLICATIONS

Notice of Reasons for Refusal drafted Jul. 1, 2024 in co-pending Japanese Patent Application 2021-538252, 6 pages.

*Primary Examiner* — Brian A Dukert
*Assistant Examiner* — Melissa A Hoban
(74) *Attorney, Agent, or Firm* — Barnes & Thornburg LLP

(57) ABSTRACT

An acetabular shell liner for use in a hip arthroplasty surgical procedure is disclosed. The acetabular shell liner includes a semi-hemispherical inner bearing layer, which includes a rim and a dome attached to the rim. The semi-hemispherical inner bearing layer includes a polymeric material having a first thickness, at an apex of the dome, and a second thickness, at the rim, that is less than the first thickness. Additionally, the acetabular shell liner includes a semi-hemispherical outer reinforcement layer mated with and encasing the dome of the semi-hemispherical inner bearing layer. The semi-hemispherical outer reinforcement layer includes a metallic material to provide structural support to the semi-hemispherical inner bearing layer.

20 Claims, 9 Drawing Sheets

(52) U.S. Cl.
CPC ... *A61F 2002/345* (2013.01); *B32B 2305/026* (2013.01); *B32B 2309/105* (2013.01); *B32B 2311/00* (2013.01); *B33Y 80/00* (2014.12)

(58) Field of Classification Search
CPC ....... B32B 9/041; B32B 15/085; B32B 15/18; B32B 27/32; B32B 2307/732; B32B 2535/00; B33Y 80/00
See application file for complete search history.

(56) References Cited

U.S. PATENT DOCUMENTS

| | | | |
|---|---|---|---|
| 3,813,699 A | 6/1974 | Giliberty | |
| 3,818,514 A | 6/1974 | Clark | |
| 3,829,904 A | 8/1974 | Ling et al. | |
| 4,524,467 A * | 6/1985 | DeCarlo, Jr. | A61F 2/32 623/19.12 |
| 4,563,778 A | 1/1986 | Roche et al. | |
| 4,619,658 A | 10/1986 | Pappas et al. | |
| 4,695,282 A | 9/1987 | Forte et al. | |
| 4,714,477 A | 12/1987 | Fichera et al. | |
| 4,892,551 A * | 1/1990 | Haber | A61F 2/32 623/23.17 |
| 4,993,410 A | 2/1991 | Kimsey | |
| 5,021,062 A | 6/1991 | Adrey et al. | |
| 5,133,763 A | 7/1992 | Mullers | |
| 5,133,765 A | 7/1992 | Cuilleron | |
| 5,147,366 A | 9/1992 | Arroyo et al. | |
| 5,156,626 A | 10/1992 | Broderick et al. | |
| 5,405,394 A | 4/1995 | Davidson | |
| 5,425,779 A | 6/1995 | Schlosser et al. | |
| 5,458,649 A | 10/1995 | Spotorno et al. | |
| 5,549,691 A | 8/1996 | Harwin | |
| 5,549,700 A * | 8/1996 | Graham | B29C 70/84 403/135 |
| 5,569,263 A | 10/1996 | Hein | |
| 5,658,338 A | 8/1997 | Tullos et al. | |
| 5,658,348 A | 8/1997 | Rohr, Jr. | |
| 5,674,225 A | 10/1997 | Mueller | |
| 5,735,905 A | 4/1998 | Parr | |
| 5,865,850 A | 2/1999 | Matthews | |
| 5,879,397 A | 3/1999 | Hartmut et al. | |
| 5,879,404 A * | 3/1999 | Bateman | A61F 2/34 623/22.21 |
| 5,885,295 A | 3/1999 | McDaniel et al. | |
| 5,888,211 A | 3/1999 | Sanders | |
| 5,938,702 A | 8/1999 | Lopez et al. | |
| 6,045,583 A | 4/2000 | Gross et al. | |
| 6,087,553 A * | 7/2000 | Cohen | A61L 27/04 623/18.11 |
| 6,110,179 A | 8/2000 | Flivik et al. | |
| 6,126,695 A | 10/2000 | Semlitsch | |
| 6,284,002 B1 | 9/2001 | Sotereanos | |
| 6,344,060 B1 | 2/2002 | Schmotzer et al. | |
| 6,368,354 B2 | 4/2002 | Burstein et al. | |
| 6,475,243 B1 | 11/2002 | Sheldon et al. | |
| 6,488,713 B1 | 12/2002 | Hershberger | |
| 6,585,771 B1 | 7/2003 | Buttermilch et al. | |
| 6,682,567 B1 * | 1/2004 | Schroeder | A61F 2/4609 623/22.24 |
| 6,826,642 B1 | 11/2004 | Reynolds | |
| 6,827,742 B2 | 12/2004 | Hayes et al. | |
| 7,160,332 B2 | 1/2007 | Frederick et al. | |
| 7,179,297 B2 | 2/2007 | McLean | |
| 7,192,449 B1 | 3/2007 | McQueen et al. | |
| 7,578,851 B2 | 8/2009 | Dong et al. | |
| 7,780,739 B2 | 8/2010 | Lakin et al. | |
| 7,794,504 B2 | 9/2010 | Case | |
| 7,819,925 B2 | 10/2010 | King et al. | |
| 7,833,276 B2 | 11/2010 | Auxepaules et al. | |
| 7,833,452 B2 | 11/2010 | Muratoglu et al. | |
| 8,100,984 B2 | 1/2012 | Lambert et al. | |
| 8,293,811 B2 | 10/2012 | Muratoglu et al. | |
| 8,308,811 B2 | 11/2012 | Newsome et al. | |
| 8,461,225 B2 | 6/2013 | Muratoglu et al. | |
| 8,652,212 B2 | 2/2014 | Rufner et al. | |
| 8,679,187 B2 | 3/2014 | Allen et al. | |
| 8,679,188 B2 | 3/2014 | Shea et al. | |
| 8,840,676 B2 | 9/2014 | Belew et al. | |
| 8,858,645 B2 | 10/2014 | Grostefon et al. | |
| 8,888,859 B2 | 11/2014 | Muratoglu et al. | |
| 8,900,319 B2 | 12/2014 | Morrey et al. | |
| 8,979,935 B2 | 3/2015 | Lozier et al. | |
| 9,044,323 B2 | 6/2015 | Nizuka et al. | |
| 9,060,865 B2 | 6/2015 | Harris et al. | |
| 9,168,683 B2 | 10/2015 | Muratoglu et al. | |
| 9,283,079 B2 | 3/2016 | Mcminn | |
| 9,339,389 B2 | 5/2016 | Tuke et al. | |
| 9,615,927 B2 | 4/2017 | Huff et al. | |
| 9,724,201 B2 | 8/2017 | Grostefon et al. | |
| 2001/0037156 A1 * | 11/2001 | Burstein | A61F 2/34 623/22.28 |
| 2002/0052661 A1 | 5/2002 | Spotorno et al. | |
| 2002/0068980 A1 * | 6/2002 | Serbousek | A61F 2/34 623/22.29 |
| 2002/0193882 A1 | 12/2002 | Koller | |
| 2003/0105529 A1 * | 6/2003 | Synder | A61F 2/34 623/22.24 |
| 2003/0144742 A1 | 7/2003 | King et al. | |
| 2003/0181987 A1 * | 9/2003 | Muirhead-Allwood | A61L 27/30 623/22.45 |
| 2003/0208280 A1 | 11/2003 | Tohidi | |
| 2004/0115172 A1 | 6/2004 | Bianchi et al. | |
| 2004/0117029 A1 | 6/2004 | Lewis et al. | |
| 2004/0199257 A1 | 10/2004 | Dooney | |
| 2004/0199260 A1 | 10/2004 | Pope et al. | |
| 2005/0143828 A1 | 6/2005 | Collins et al. | |
| 2005/0146070 A1 | 7/2005 | Muratoglu et al. | |
| 2006/0009857 A1 | 1/2006 | Gibbs et al. | |
| 2006/0149386 A1 | 7/2006 | Clarke et al. | |
| 2007/0005144 A1 | 1/2007 | Leisinger et al. | |
| 2007/0032877 A1 | 2/2007 | Whiteside | |
| 2007/0100464 A1 | 5/2007 | Meulink | |
| 2007/0106392 A1 | 5/2007 | Servidio et al. | |
| 2007/0118227 A1 | 5/2007 | King et al. | |
| 2007/0142914 A1 * | 6/2007 | Jones | B23K 26/382 623/14.13 |
| 2007/0179629 A1 | 8/2007 | Murphy | |
| 2007/0198096 A1 | 8/2007 | Wort | |
| 2007/0250175 A1 | 10/2007 | Meridew et al. | |
| 2008/0071381 A1 | 3/2008 | Buscher et al. | |
| 2008/0172130 A1 | 7/2008 | Macara | |
| 2008/0208350 A1 | 8/2008 | Roger | |
| 2008/0215142 A1 | 9/2008 | Muratoglu et al. | |
| 2008/0215158 A1 | 9/2008 | Pope et al. | |
| 2009/0005879 A1 | 1/2009 | Tuke et al. | |
| 2009/0036993 A1 | 2/2009 | Metzger | |
| 2009/0088864 A1 * | 4/2009 | Lewis | A61F 2/34 623/22.32 |
| 2009/0265009 A1 | 10/2009 | Ward et al. | |
| 2010/0082101 A1 | 4/2010 | Muratoglu et al. | |
| 2010/0131073 A1 | 5/2010 | Meridew et al. | |
| 2010/0174380 A1 * | 7/2010 | Lewis | A61F 2/32 623/22.11 |
| 2010/0234964 A1 | 9/2010 | Yoon et al. | |
| 2010/0241239 A1 | 9/2010 | Smith | |
| 2011/0015752 A1 | 1/2011 | Meridew | |
| 2011/0153025 A1 * | 6/2011 | McMinn | B32B 15/08 427/2.24 |
| 2011/0247229 A1 | 10/2011 | Anapliotis et al. | |
| 2012/0016485 A1 * | 1/2012 | Sharp | A61B 17/8066 623/22.21 |
| 2012/0089235 A1 | 4/2012 | Conway et al. | |
| 2012/0185059 A1 | 7/2012 | Vankoski et al. | |
| 2012/0319332 A1 | 12/2012 | Mcminn | |
| 2013/0060344 A1 | 3/2013 | Pierce | |
| 2013/0073051 A1 | 3/2013 | Meridew | |
| 2013/0190889 A1 | 7/2013 | Li et al. | |
| 2013/0204389 A1 | 8/2013 | Kumar et al. | |
| 2013/0218288 A1 * | 8/2013 | Fonte | A61F 2/28 623/23.5 |

(56) References Cited

U.S. PATENT DOCUMENTS

| | | |
|---|---|---|
| 2013/0245775 A1 | 9/2013 | Metcalfe |
| 2013/0297036 A1 | 11/2013 | Collins |
| 2013/0325139 A1 | 12/2013 | Steiner et al. |
| 2014/0156018 A1 | 6/2014 | Allen et al. |
| 2014/0303742 A1 | 10/2014 | Prybyla et al. |
| 2014/0324183 A1 | 10/2014 | Springer et al. |
| 2014/0324184 A1 | 10/2014 | Bigsby et al. |
| 2015/0025647 A1 | 1/2015 | Zhang |
| 2015/0073560 A1* | 3/2015 | Shavit .................. A61F 2/30767 623/18.11 |
| 2015/0250596 A1 | 9/2015 | Whitaker et al. |
| 2015/0351918 A1 | 12/2015 | Currier et al. |
| 2015/0359638 A1* | 12/2015 | Khowaylo .............. A61L 27/06 623/18.11 |
| 2016/0015520 A1* | 1/2016 | Smith ...................... A61F 2/34 29/592 |
| 2016/0030182 A1 | 2/2016 | Mcminn |
| 2016/0074167 A1 | 3/2016 | Vautrin |
| 2016/0296289 A1* | 10/2016 | Choudhury ............ B33Y 10/00 |
| 2018/0228616 A1* | 8/2018 | Piecuch ................ B33Y 80/00 |
| 2020/0205988 A1* | 7/2020 | Behzadi ............ A61B 17/7283 |

FOREIGN PATENT DOCUMENTS

| | | |
|---|---|---|
| CN | 101883540 A | 11/2010 |
| CN | 102458311 A | 5/2012 |
| CN | 203873917 U | 10/2014 |
| CN | 107550604 A | 1/2018 |
| DE | 10335442 A1 | 2/2005 |
| DE | 102008030260 A1 | 12/2009 |
| EA | 010647 B1 | 10/2008 |
| EP | 0207873 A1 | 1/1987 |
| EP | 0342014 A1 | 11/1989 |
| EP | 556926 A1 | 8/1993 |
| EP | 430831 B1 | 8/1994 |
| EP | 0663194 A1 | 7/1995 |
| EP | 761242 A1 | 3/1997 |
| EP | 0807426 A2 | 11/1997 |
| EP | 821922 A1 | 2/1998 |
| EP | 655230 B1 | 9/1999 |
| EP | 1293179 A1 | 3/2003 |
| EP | 901777 B1 | 5/2003 |
| EP | 1359950 A1 | 11/2003 |
| EP | 695153 B1 | 4/2004 |
| EP | 1442725 A2 | 8/2004 |
| EP | 1057461 B1 | 11/2005 |
| EP | 1433443 B1 | 7/2006 |
| EP | 1685809 A2 | 8/2006 |
| EP | 1223895 B1 | 12/2006 |
| EP | 1408886 B1 | 3/2007 |
| EP | 1767170 A2 | 3/2007 |
| EP | 1091705 B1 | 8/2007 |
| EP | 1815825 A1 | 8/2007 |
| EP | 1825834 A1 | 8/2007 |
| EP | 1421918 B1 | 4/2008 |
| EP | 1647242 B1 | 5/2008 |
| EP | 2165682 A2 | 3/2010 |
| EP | 2198808 A1 | 6/2010 |
| EP | 1312323 B1 | 8/2011 |
| EP | 1825834 B1 | 12/2011 |
| EP | 2405864 A2 | 1/2012 |
| EP | 1841686 B1 | 2/2012 |
| EP | 2140835 B1 | 8/2012 |
| EP | 1253870 B1 | 3/2013 |
| EP | 2574310 A2 | 4/2013 |
| EP | 2193764 B1 | 9/2013 |
| EP | 2214736 B1 | 3/2014 |
| EP | 2162096 B1 | 2/2015 |
| EP | 2106249 B1 | 8/2015 |
| EP | 1722719 B1 | 4/2016 |
| EP | 2129335 B1 | 4/2016 |
| FR | 1481424 A | 5/1967 |
| FR | 2105998 A5 | 4/1972 |
| GB | 1485295 A | 9/1977 |
| GB | 2042897 A | 10/1980 |
| GB | 2152385 A | 8/1985 |
| JP | 11155890 A | 6/1999 |
| JP | 3172112 B2 | 6/2001 |
| JP | 2001507273 A | 6/2001 |
| JP | 2002345858 A | 12/2002 |
| JP | 2003175061 A | 6/2003 |
| JP | 4051950 B2 | 2/2008 |
| JP | 2013536009 A | 9/2013 |
| JP | 6007386 B2 | 10/2016 |
| RU | 2290901 C1 | 1/2007 |
| RU | 2309706 C2 | 11/2007 |
| WO | 9222265 A1 | 12/1992 |
| WO | 9313733 A1 | 7/1993 |
| WO | 9515132 A1 | 6/1995 |
| WO | 9522944 A1 | 8/1995 |
| WO | 9603931 A1 | 2/1996 |
| WO | 9922674 A1 | 5/1999 |
| WO | 03049649 A1 | 6/2003 |
| WO | 03084432 A2 | 10/2003 |
| WO | 2004069096 A2 | 8/2004 |
| WO | 2006011028 A1 | 2/2006 |
| WO | 2008117056 A1 | 10/2008 |
| WO | 2008128282 A1 | 10/2008 |
| WO | 2008146121 A2 | 12/2008 |
| WO | 2009106867 A1 | 9/2009 |
| WO | 2008080595 A2 | 10/2009 |
| WO | 2010089555 A2 | 8/2010 |
| WO | 2010129880 A2 | 11/2010 |
| WO | 2012015945 A2 | 2/2012 |
| WO | 2012035294 A2 | 3/2012 |
| WO | 2014087177 A1 | 6/2014 |
| WO | 2014114944 A1 | 7/2014 |
| WO | 2016200735 A1 | 12/2016 |
| WO | 2017003570 A1 | 1/2017 |
| WO | 2017053183 A1 | 3/2017 |

\* cited by examiner

METAL REINFORCED ACETABULAR SHELL LINER

TECHNICAL FIELD

The present disclosure relates generally to orthopaedic prosthetic components and, more particularly, to acetabular prosthetic components.

BACKGROUND

Joint arthroplasty is a surgical procedure in which a patient's natural joint is replaced by a prosthetic joint. In a hip arthroplasty procedure, at least a portion of a patient's hip ball and socket joint is replaced with one or more corresponding prosthetic components. For example, the socket portion of the joint, known as the acetabulum, may be replaced with one or more acetabular prosthetic components (e.g., an acetabular shell that fits within the acetabulum and a liner that fits within the shell to act as a bearing surface). Similarly, the ball portion of the joint, known as the femoral head, may be replaced with a femoral head prosthetic component.

In recent years, it has been determined that decreasing the differential between the outer diameter of the acetabular prosthetic component (e.g., the acetabular shell) and the outer diameter of the femoral head prosthetic component can produce enhanced results in certain patients.

SUMMARY

In one aspect, the present disclosure includes an acetabular shell liner for use in a hip arthroplasty surgical procedure. The acetabular shell liner includes a semi-hemispherical inner bearing layer, which includes a rim and a dome attached to the rim. The semi-hemispherical inner bearing layer includes a polymeric material having a first thickness, at an apex of the dome, and a second thickness, at the rim, that is less than the first thickness. Additionally, the acetabular shell liner includes a semi-hemispherical outer reinforcement layer mated with and encasing the dome of the semi-hemispherical inner bearing layer. The semi-hemispherical outer reinforcement layer includes a metallic material to provide structural support to the semi-hemispherical inner bearing layer.

In some embodiments of the acetabular shell liner, the first thickness is less than four millimeters. The metallic material of the acetabular shell liner, in some embodiments, has a thickness of approximately 0.5 millimeters. In some embodiments, the semi-hemispherical outer reinforcement layer includes a concave inner wall having a porous surface engaged with the polymeric material of the semi-hemispherical inner bearing layer. The semi-hemispherical outer reinforcement layer of the acetabular shell liner may be 3D printed. Additionally or alternatively, the porous surface may be a coating on the metal material of the semi-hemispherical outer reinforcement layer. The metallic material may include at least one of titanium, cobalt chromium, stainless steel, or medium grade high strength steel. In some embodiments, the semi-hemispherical inner bearing layer may be compression molded onto the semi-hemispherical outer reinforcement layer. In other embodiments, the semi-hemispherical inner bearing layer may be injection molded onto the semi-hemispherical outer reinforcement layer. The semi-hemispherical outer reinforcement layer may be shaped to fit into an acetabular shell of a modular acetabular prosthesis system and the semi-hemispherical inner bearing layer may be shaped to receive a head of a femoral prosthesis.

In another aspect, the present disclosure includes a modular acetabular prosthesis. The modular acetabular prosthesis includes an acetabular shell shaped to fit in a surgically prepared acetabulum of a patient. Additionally, the acetabular prosthesis includes an acetabular shell liner. The acetabular shell liner includes a semi-hemispherical inner bearing layer that includes a rim and a dome attached to the rim. The semi-hemispherical inner bearing layer includes a polymeric material. The acetabular shell liner also includes a semi-hemispherical outer reinforcement layer mated with and encasing the dome of the semi-hemispherical inner bearing layer. The semi-hemispherical outer reinforcement layer includes a metallic material to provide structural support to the semi-hemispherical inner bearing layer. Additionally, the semi-hemispherical outer reinforcement layer is shaped to fit into the acetabular shell.

In some embodiments of the modular acetabular prosthesis, the polymeric material of the semi-hemispherical inner bearing layer has a thickness, at an apex of the dome, that is less than four millimeters. Additionally, the metallic material of the semi-hemispherical outer reinforcement layer may have a thickness of approximately 0.5 millimeters. The semi-hemispherical outer reinforcement layer may include a concave inner wall having a porous surface engaged with the polymeric material of the semi-hemispherical inner bearing layer. In some embodiments, the semi-hemispherical outer reinforcement layer is 3D printed. Additionally or alternatively, the porous surface may be a coating on the metal material of the semi-hemispherical outer reinforcement layer. The metallic material of the semi-hemispherical outer reinforcement layer may include at least one of titanium, cobalt chromium, stainless steel, or medium grade high strength steel.

In yet another aspect, the present disclosure includes a method for using a modular acetabular prosthesis in a hip arthroplasty surgical procedure. The method includes inserting an acetabular shell into a surgically prepared acetabulum of a patient. The method also includes securing, into the acetabular shell, a liner that includes a polymeric semi-hemispherical inner layer that is at least partially encased in a metal semi-hemispherical outer reinforcement layer. The method may also include fitting a head of a femoral prosthesis into a cavity defined by the polymeric semi-hemispherical inner layer of the liner.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
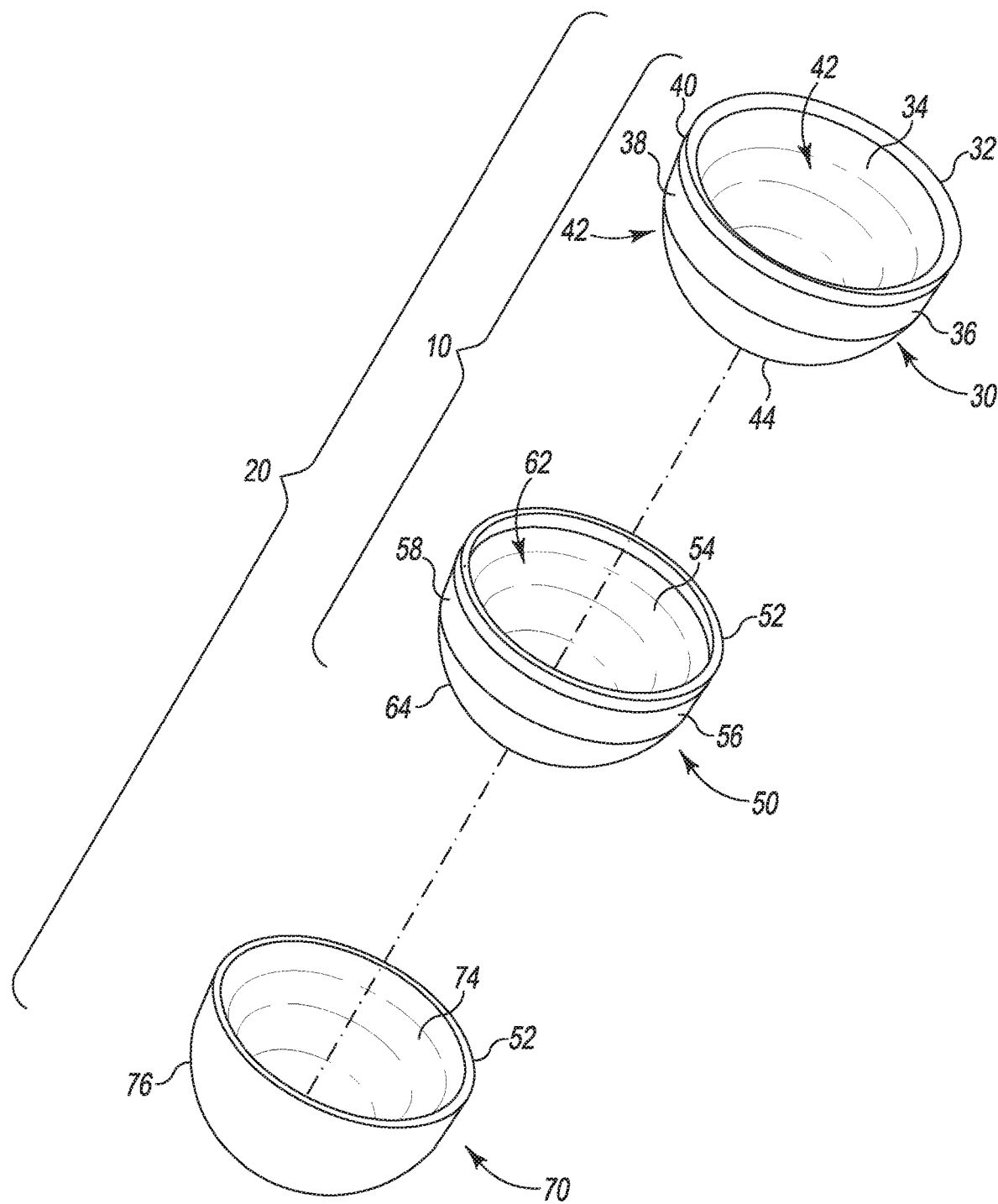
FIG. 1 is an exploded perspective view of an embodiment of a modular acetabular prosthesis having a metal reinforced acetabular shell liner.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an illustrative modular acetabular prosthesis 20 includes a metal reinforced acetabular shell liner 10 and an acetabular shell 70. In use, as discussed in more detail below, the metal reinforced acetabular shell liner 10 is configured to be received in the acetabular shell 70 and forms a bearing surface for a corresponding femoral component. As shown, the metal reinforced acetabular shell liner 10 includes a semi-hemispherical (i.e., generally hemispherical in shape but not necessarily defining a perfect hemisphere) inner bearing layer 30 and a semi-hemispherical outer reinforcement layer 50 or sleeve. In the illustrative embodiment, the semi-hemispherical inner bearing layer 30 includes a rim 32 and a dome 44 attached to the rim 32. The dome 44 is defined by, or otherwise includes, a concave inner wall 34 and a convex outer wall 36 opposite the concave inner wall 34. The concave inner wall 34 extends inwardly from the rim 32 to define a cavity 42, sized and shaped to receive a head of a femoral prosthesis component, and the convex outer wall 36 extends from the rim 32 and defines an outer surface of the dome 44. As shown in FIG. 1, the rim 32 includes a substantially cylindrical portion 38, which is attached to or integral with the dome 44, and a rim edge 40.

As described in more detail herein, the inner bearing layer 30, in the illustrative embodiment, is made of a polymeric material such as polyethylene (e.g., ultra-high-molecular-weight polyethylene (UHMWPE)), though in other embodiments, the inner bearing layer 30 may be made from a different material (e.g., ceramic). The material (e.g., polymeric material) of the inner bearing layer 30 may be thinner near the rim 32 (e.g., the rim edge 40) and thicker at an apex 46 of the dome 44, as shown in more detail with respect to FIGS. 5 and 6.

The inner bearing layer 30 is mated with, or otherwise attached to, the semi-hemispherical outer reinforcement layer 50, which is made of metal (e.g., titanium, cobalt chromium, stainless steel, and/or medium grade high strength steel) and is comparatively much thinner than the inner bearing layer 30. The metal construction enables the outer reinforcement layer 50 to provide structural reinforcement to the polymer inner bearing layer 30 thereby allowing thinner polymer inner bearing layers to be utilized relative to the case of an unreinforced polymer inner bearing layer. As such, due to the reduction in the amount of material (e.g., the overall thickness of the liner 10) between the femoral head and the acetabular shell 70, a larger femoral head can be used with an acetabular shell 70 of a given size (the outer diameter of which is limited by the size of the patient's acetabulum) relative to the size of the head that could be used with the same shell in conjunction with a thicker liner. In some patients, such a pairing of implant components may provide enhanced results.

Still referring to FIG. 1, the outer reinforcement layer 50 is similar in shape to the inner bearing layer 30, in that the outer reinforcement layer 50 is semi-hemispherical, includes a rim 52, a concave inner wall 54 extending inwardly from the rim 52 to define a cavity 62, and a convex outer wall 56 opposite the inner wall 54. Further, the outer reinforcement layer 50 includes a dome 64 that is defined by, or otherwise includes, the concave inner wall 54 and the convex outer wall 56. The rim 52 includes a substantially cylindrical portion 58, which is attached to or integral with the dome 64 and a rim edge 60. In the illustrative embodiment, the substantially cylindrical portion 58 may be tapered by a predefined amount (e.g., ten degrees), such that the diameter near the rim 52 (e.g., the rim edge 60) is greater than the diameter near the dome 64. The taper may help the acetabular liner 10 lock into the acetabular shell 70 when the liner 10 is pressed into the acetabular shell 70 during a hip arthroplasty procedure.

During manufacture, in the illustrative embodiment, the inner bearing layer 30 is molded onto the outer reinforcement layer 50 (e.g., via injection molding or compression molding), such that the outer reinforcement layer 50 encases and provides structural support to the comparatively softer inner bearing layer 30. Further, in the illustrative embodiment, the inner wall 54 of the outer reinforcement layer 50 is porous, to help the polymeric material of the inner bearing layer 30 securely mate with (e.g., interdigitate with, affix to, etc.) the inner wall 54. For example, in some embodiments, during the molding process, the polymeric material of the inner bearing layer 30 is forced into or otherwise interdigitated with the porous surface of the inner wall 54, thereby enhancing a mechanical connection therebetween.

In some embodiments, the porosity of the inner wall 54 is provided by a porous coating. One type of porous coating is Porocoat® Porous Coating which is commercially available from DePuy Synthes Products, Inc. of Warsaw, Indiana. In other embodiments, the porosity may be an inherent feature of the inner wall 54, resulting from the process by which the outer reinforcement layer 50 was manufactured. For example, in some embodiments, the outer reinforcement layer 50 may be 3D (three dimensionally) printed to produce porosity in the walls 54, 56. Still referring to FIG. 1, the acetabular liner 10 is sized and shaped to be fitted into an acetabular shell 70, after the acetabular shell 70 has been inserted into a patient's surgically prepared acetabulum. The acetabular shell 70 may be embodied as a typical acetabular shell prosthesis and is illustratively semi-hemispherical and includes a rim 72, a concave inner wall 74 that extends inwardly from the rim 72, and a convex outer wall 76 opposite the inner wall 74.

Figure 2:
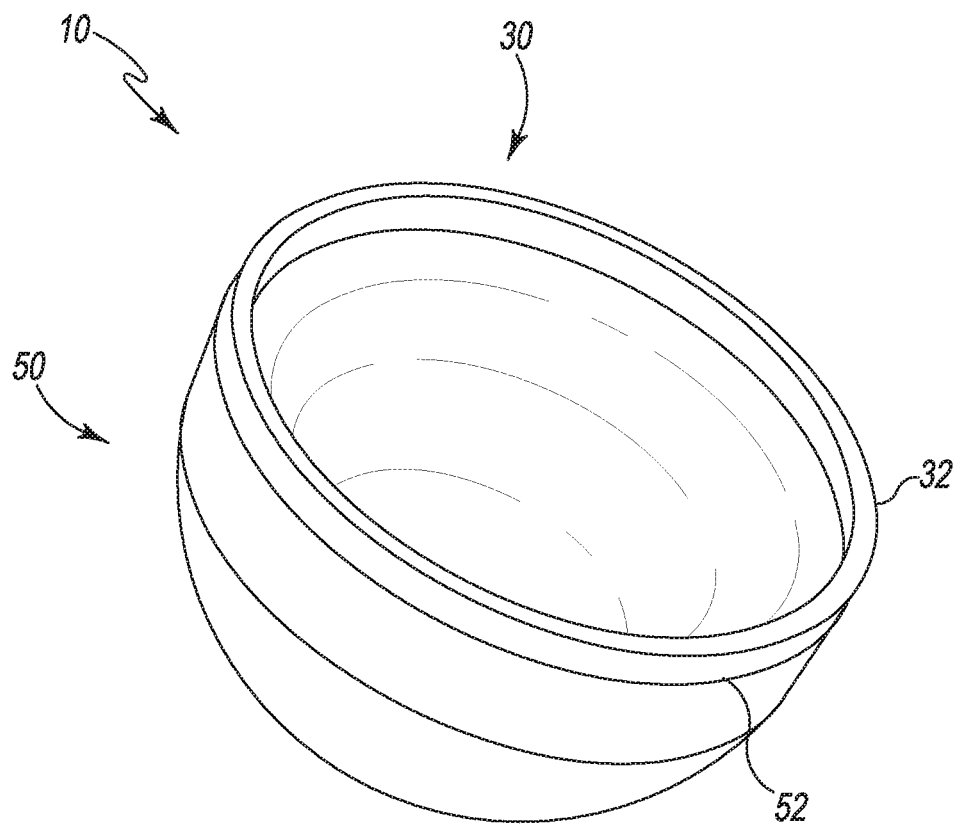
FIG. 2 is a perspective view of the metal reinforced acetabular shell liner of FIG. 1.

Referring now to FIG. 2, the acetabular shell liner 10 is shown in its manufactured form. As shown, the inner bearing layer 30 is mated with the outer reinforcement layer 50. In the illustrative embodiment, the rim 32 of the inner bearing layer 30 extends past the rim 52 of the outer reinforcement layer 50. In other words, in the illustrative embodiment, the outer reinforcement layer 50 does not encase the entire inner bearing layer 30. The portion of the polymeric inner bearing layer 30 that extends past the rim 52 of the outer reinforcement layer 50 may act as a buffer that reduces the potential of metal-on-metal contact between the femoral prosthesis and the acetabular prosthesis 20 (e.g., the rims 52, 72), when the prosthetic joint is flexed.

Figure 3:
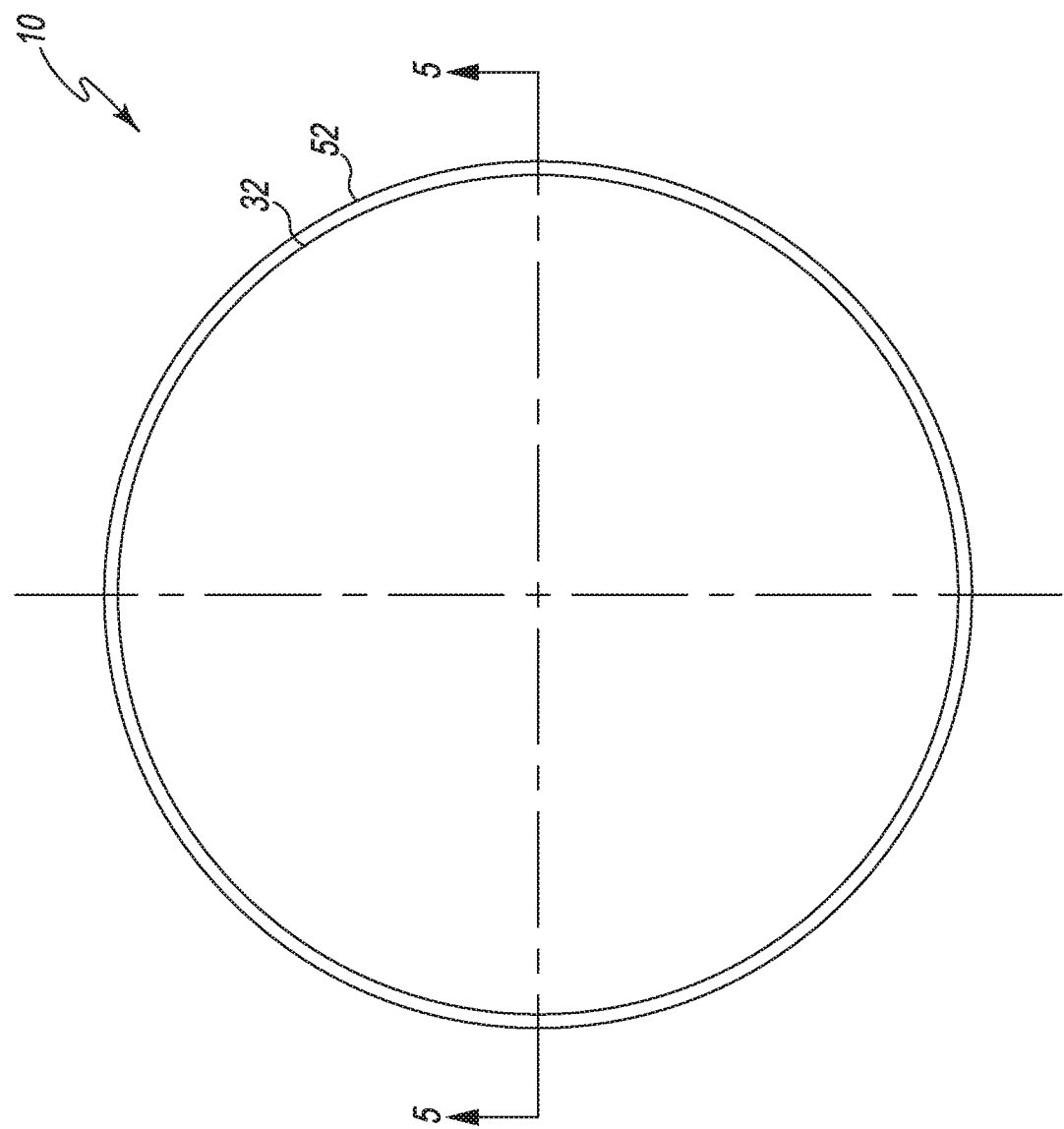
FIG. 3 is a plan view of the metal reinforced acetabular shell liner of FIG. 1.
Figure 4:
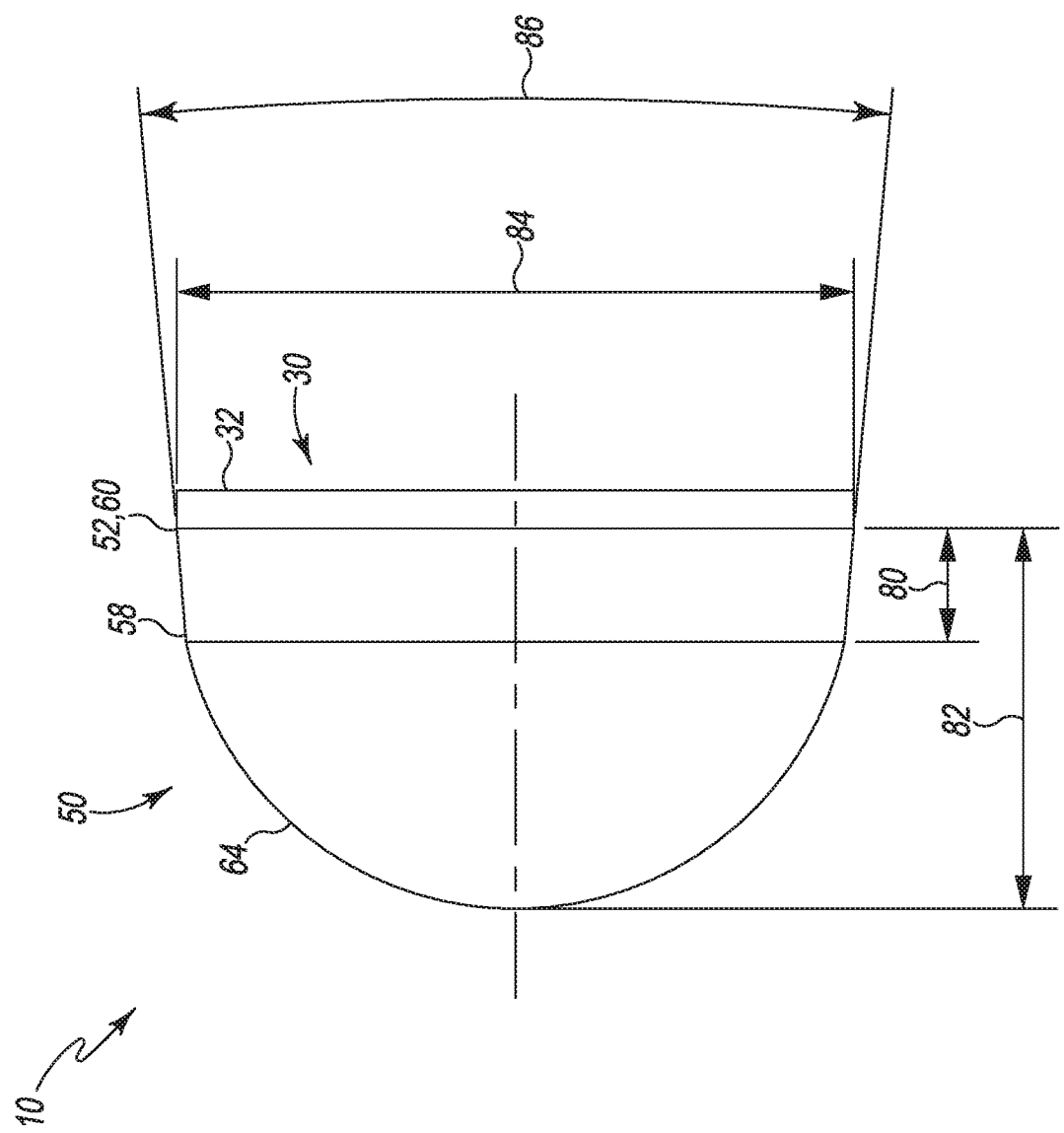
FIG. 4 is an elevation view of the metal reinforced acetabular shell liner of FIG. 1.

Referring now to FIGS. 3 and 4, it can be seen that the diameter 84 of the rim 32 of the inner bearing layer 30 is slightly less than the diameter of the rim 52. As mentioned above, the substantially cylindrical portion 58 of the outer reinforcement layer 50 is tapered from the rim edge 60 to the dome 64 by a predefined angle 86 (e.g., 10 degrees). The tapered shape enables the liner 10 to taper lock or otherwise be secured into the acetabular shell 70 when the liner 10 is pressed into the acetabular shell 70 (e.g., by a surgeon). In some embodiments, and as shown more clearly in FIGS. 5 and 6, the rim 32 may have a chamfer to provide clearance between the rim 32 and the rim 52 (e.g., to help the rim 52 lock into the acetabular shell 70).

Figure 5:
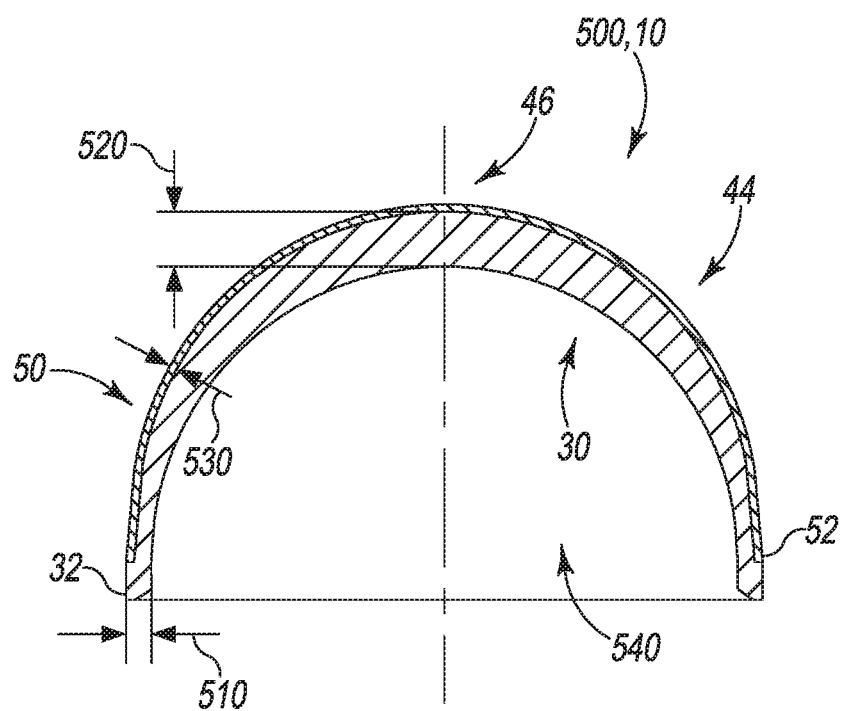
FIG. 5 is a cross-sectional elevation view of one embodiment of the metal reinforced acetabular shell liner of FIG. 1 taken generally along line 5-5 of FIG. 3.

Referring now to FIG. 5, a generally cross-sectional view of one embodiment 500 of the acetabular shell liner 10 taken along line 5-5 of FIG. 3, and rotated by 180 degrees, is shown. In the embodiment 500, a thickness 510 of the inner bearing layer 30 near the rim 32 is less than a thickness 520 of the inner bearing layer 30 at the apex 46 of the dome 44. In the illustrative embodiment, the change in thickness of the inner bearing layer 30 is gradual, to provide a smooth inner surface for the femoral head to bear against. The thickness 520 of the polymeric material at the apex 46, in the embodiment 500, is less than 4 millimeters (e.g., approximately 3.3 millimeters). The metal outer reinforcement layer 50, by contrast, is much thinner than either of the thicknesses 510, 520, at approximately 0.5 millimeters.

The thicknesses of the inner bearing layer 30 and the outer reinforcement layer 50, taken together, result in a combined thickness that is significantly thinner than typical acetabular shell liners. As such, the embodiment 500 provides a cavity 540 that can accommodate a much larger femoral head for a given acetabular shell size than typical acetabular shell and liner assemblies, while providing the structural integrity afforded by much thicker acetabular shell and liner assemblies (which are unable to accommodate as large of a femoral head). In the embodiment 500, the ratio of the acetabular shell diameter to femoral head diameter is approximately 46 millimeters to 36 millimeters (i.e., a differential of 10 millimeters).

Figure 6:
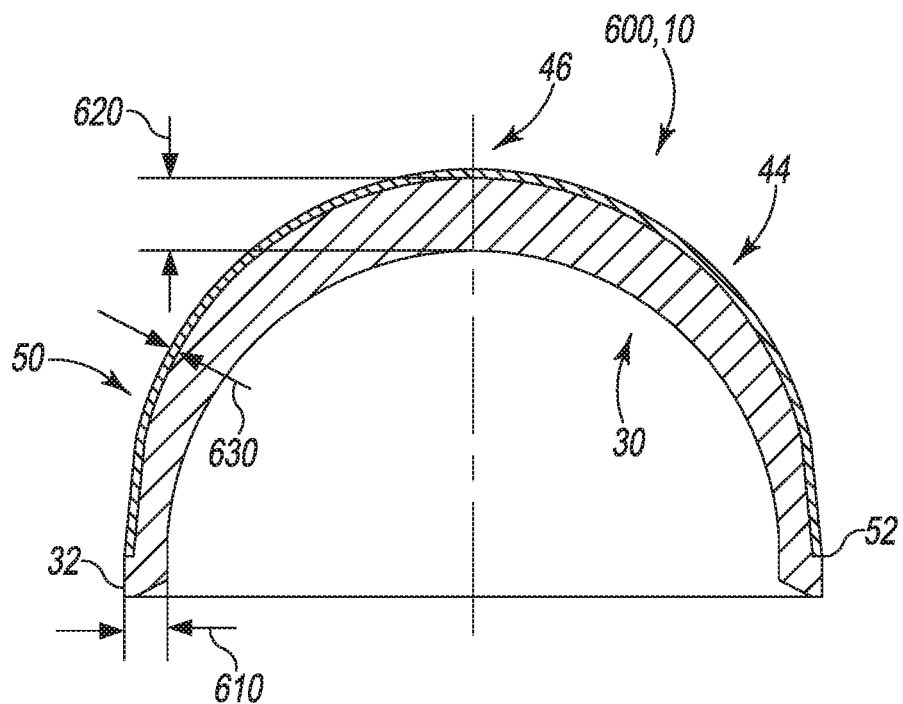
FIG. 6 is a cross-sectional elevation view of another embodiment of the metal reinforced acetabular shell liner of FIG. 1 taken generally along line 5-5 of FIG. 3.

Referring now to FIG. 6, a generally cross-sectional view along line 5-5 of FIG. 3, of another embodiment 600 of the acetabular shell liner 10 is shown. The embodiment 600 is similar to the embodiment 500, in that the thickness of the inner bearing layer 30 increases from one thickness 610 near the rim 32 to another thickness 620 at the apex 46. In the embodiment 600, the thickness 620 is approximately 4.32 millimeters. Similar to the embodiment 500, the thickness 630 of the outer reinforcement layer 50 in the embodiment 600 is approximately 0.5 millimeters. In the embodiment 600, the ratio of the acetabular shell diameter to femoral head diameter is approximately 48 millimeters to 36 millimeters (i.e., a differential of 12 millimeters).

Figure 7:
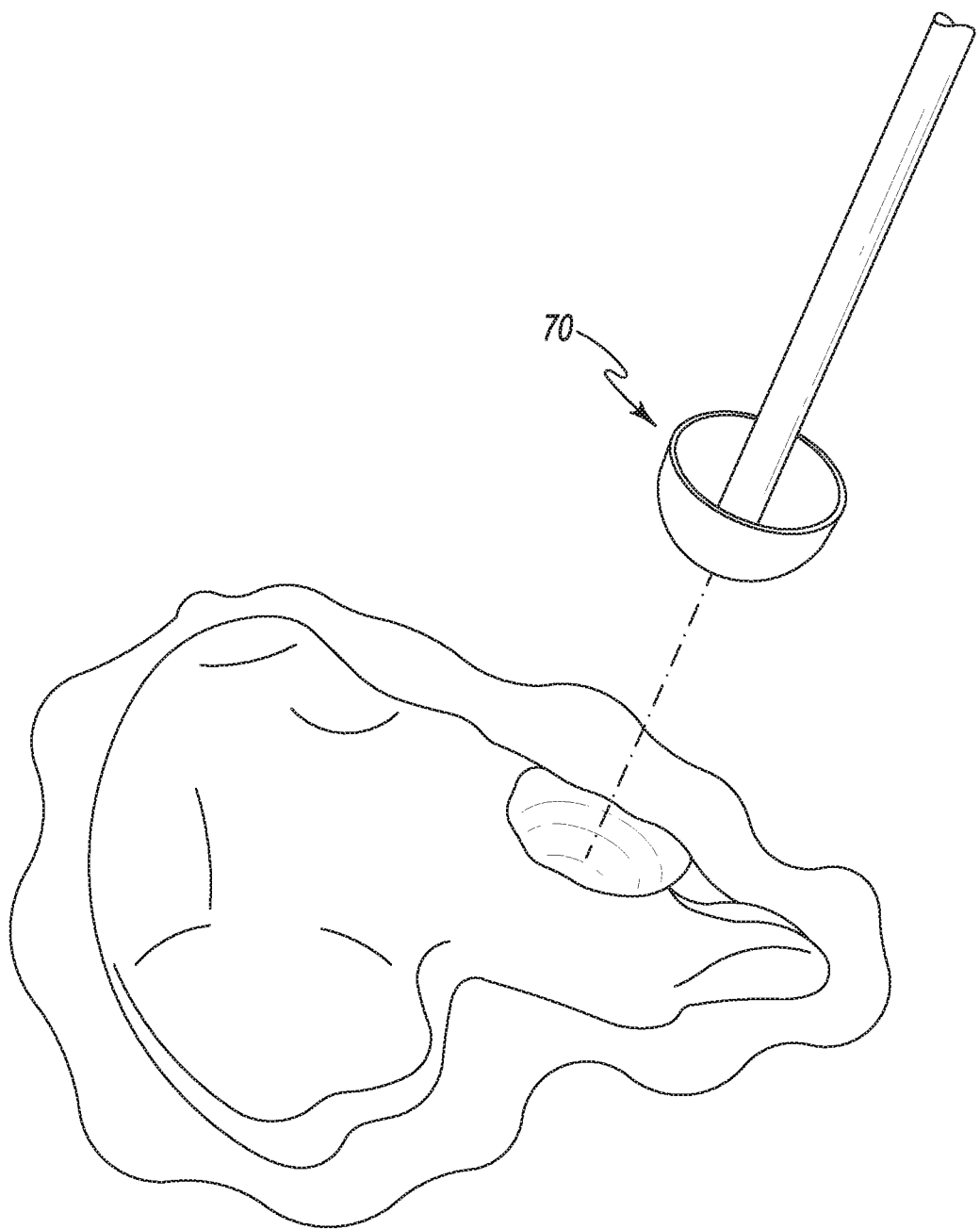
FIG. 7 is a perspective view of a patient's acetabulum with an acetabular shell being advanced towards the acetabulum.

Referring now to FIG. 7, a method for using the modular acetabular prosthesis 20 in a hip arthroplasty procedure may begin with a surgeon inserting the acetabular shell 70 into a surgically prepared (e.g., by a surgical reamer) acetabulum of a patient. The surgeon may press fit the acetabular shell 70 into place using a driver tool. In some embodiments, the surgeon may additionally thread one or more screws through one or more bores in the acetabular shell 70 to further secure the shell 70 in the acetabulum. In yet other embodiments, the surgeon may utilize other techniques, such as use of bone cement, to insert the shell 70 into the acetabulum.

Figure 8:
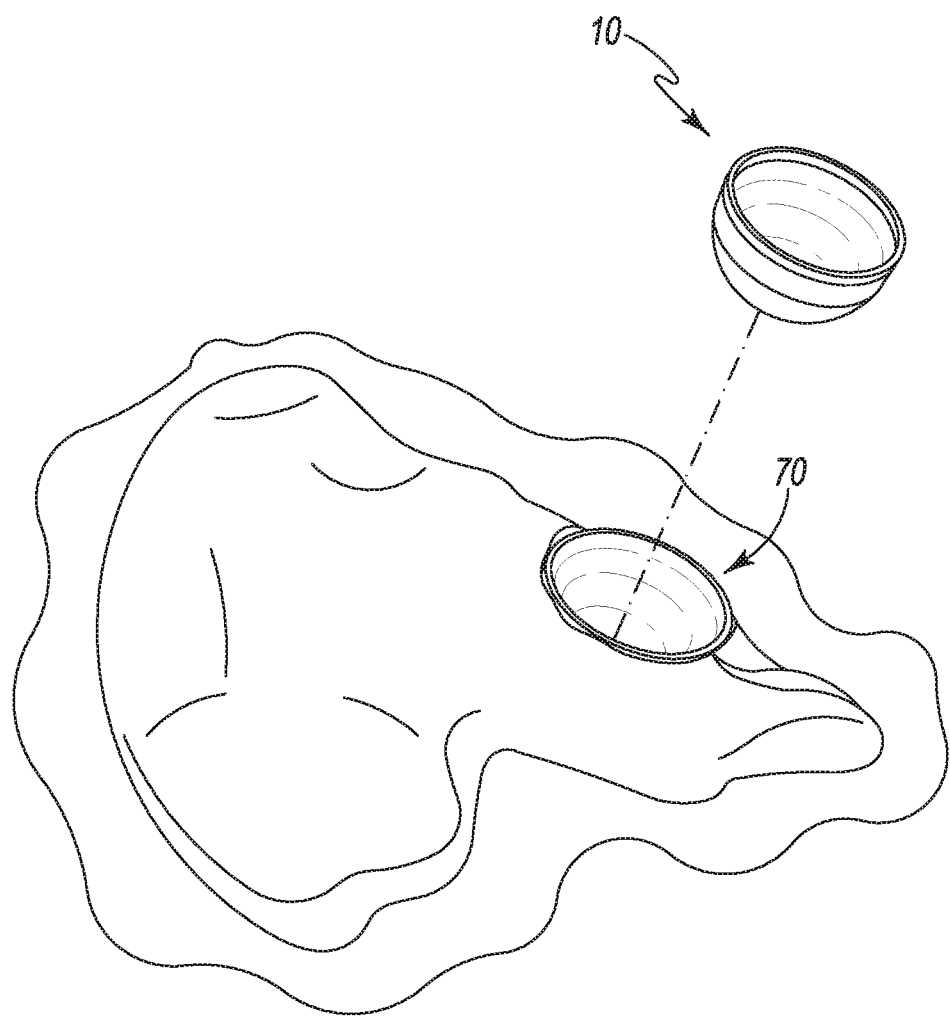
FIG. 8 is a perspective view of the patient's acetabulum with the acetabular shell inserted into the acetabulum and the metal reinforced acetabular shell liner being advanced towards the acetabular shell.

Referring now to FIG. 8, the surgeon may subsequently secure, into the acetabular shell 70 (which has been inserted into the acetabulum, as described above) a liner (e.g., the acetabular shell liner 10) that includes a polymeric semi-hemispherical inner layer (e.g., the inner bearing layer 30) that is at least partially encased in a metal semi-hemispherical outer reinforcement layer (e.g. the outer reinforcement layer 50). As described above, the liner 10, in the illustrative embodiment, is shaped to lock into the acetabular shell 70 (e.g., due to the tapered cylindrical portion 58 of the outer reinforcement layer 50). Additionally or alternatively, in some embodiments, the liner 10 may be secured into the acetabular shell 70 using another mechanism (e.g., one or more mechanical locking mechanisms).

Figure 9:
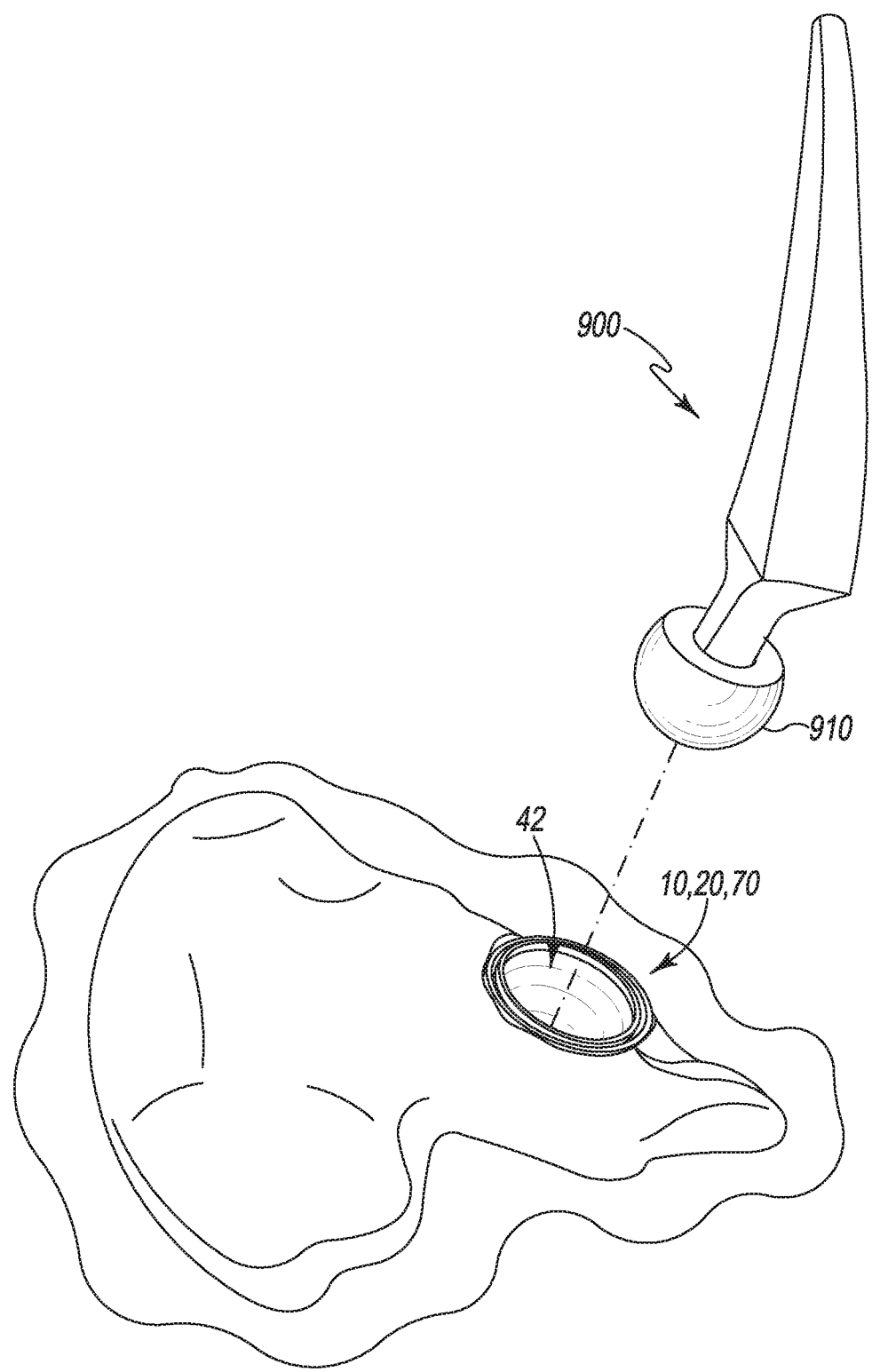
FIG. 9 is a perspective view of the patient's acetabulum with the acetabular shell and liner inserted and a femoral prosthesis component being advanced towards a cavity in the liner.
Figure 10:
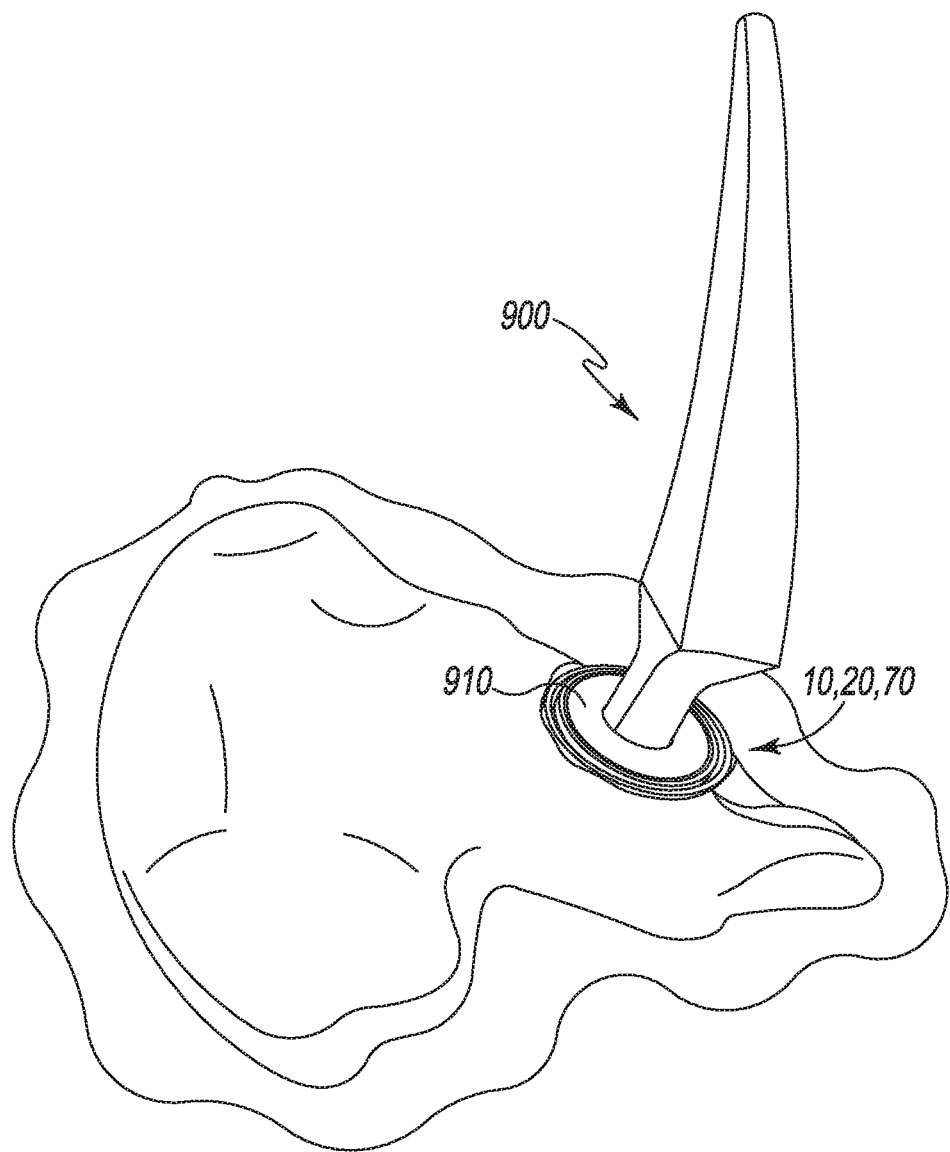
FIG. 10 is a perspective view of the femoral prosthesis fitted into the liner.

Referring now to FIGS. 9 and 10, with the acetabular shell 70 and acetabular shell liner 10 in the patient's acetabulum, the surgeon may fit a head 910 of a femoral prosthesis 900 into a cavity (e.g., the cavity 42) defined by the polymeric semi-hemispherical inner layer (e.g., the inner bearing layer 30) of the liner 10. As described above, the head 910 of the femoral prosthesis 900 is larger (e.g., in diameter) than would be possible with typical acetabular shell and liner assemblies because the combined thickness of the polymeric semi-hemispherical inner layer (e.g., the inner bearing layer 30) and the metal semi-hemispherical outer reinforcement layer (e.g., the outer reinforcement layer 50) is thinner than typical liners while providing at least as much structural integrity as thicker liners.

In subsequent steps, the surgeon may test the fit and range of motion of the femoral head 910 in the modular acetabular prosthesis 20. In some embodiments, the acetabular shell 70 and/or liner 10 may be trial components (e.g., instruments) that the surgeon may swap out with other trial acetabular shells and/or liners having the features described herein, before determining that a particular combination of acetabular shell and liner provides a satisfactory fit and range of motion. Afterwards, the surgeon may replace the trial components (e.g., instruments) with permanent implant versions of the components.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic implant for use in a hip arthroplasty surgical procedure, comprising:
    a liner component configured to be secured to an acetabular shell component, comprising:
        a semi-hemispherical metallic outer reinforcement layer having a first dome and a first rim attached to the first dome, the first rim including a tapered portion having an outer wall that extends outwardly from the first dome to a distal edge of the first rim at a predefined angle, and
        a semi-hemispherical polymeric inner bearing layer molded to the metallic outer reinforcement layer, the polymeric inner bearing layer having a second rim and a second dome extending away from the second rim, wherein, at an apex of the second dome, the thickness of the polymeric inner bearing layer is less than 4.0 millimeters and wherein the second rim (i) includes an inner wall and an outer wall parallel with the inner wall, (ii) extends past and wraps onto the first rim of the semi-hemispherical metallic outer reinforcement layer, (iii) and includes a distal edge that is chamfered inwardly.

2. The orthopaedic implant of claim 1, wherein, at the apex of the second dome, the thickness of the polymeric inner bearing layer is less than 3.5 millimeters.

3. The orthopaedic implant of claim 1, wherein the metallic outer reinforcement layer has a thickness of approximately 0.5 millimeters.

4. The orthopaedic implant of claim 1, wherein the metallic outer reinforcement layer comprises a concave inner wall having a porous surface to which the polymeric inner bearing layer is molded.

5. The orthopaedic implant of claim 4, wherein the metallic outer reinforcement layer is 3D printed.

6. The orthopaedic implant of claim 4, wherein the porous surface is a coating on the metallic outer reinforcement layer.

7. The orthopaedic implant of claim 1, wherein the metallic outer reinforcement layer is constructed of at least one of titanium, cobalt chromium, stainless steel, or medium grade high strength steel.

8. The orthopaedic implant of claim 1, wherein the polymeric inner bearing layer is compression molded onto the semi-hemispherical outer reinforcement layer.

9. The orthopaedic implant of claim 1, wherein the polymeric inner bearing layer is injection molded onto the metallic outer reinforcement layer.

10. The orthopaedic implant of claim 1, wherein the metallic outer reinforcement layer is configured to be taper fit to the acetabular shell component.

11. The orthopaedic implant of claim 1, wherein the polymeric inner bearing layer is configured to receive a head of a femoral prosthesis.

12. A modular acetabular prosthesis comprising:
    an acetabular shell component shaped to fit in a surgically-prepared acetabulum of a patient; and
    a liner component secured to the acetabular shell component, the liner component, comprising:
        a semi-hemispherical metallic outer reinforcement layer configured to engage a concave inner wall of the acetabular shell component, and
        a semi-hemispherical polymeric inner bearing layer molded to the metallic outer reinforcement layer, the semi-hemispherical polymeric inner bearing layer including a cylindrical rim and a dome extending away from the cylindrical rim, wherein the cylindrical rim includes an inner wall and an outer wall parallel with the inner wall and wherein the cylindrical rim extends past and wraps onto a rim of the semi-hemispherical metallic outer reinforcement layer.

13. The modular acetabular prosthesis of claim 12, wherein:
    at an apex of the dome, the thickness of the polymeric inner bearing layer is less than 4.0 millimeters.

14. The modular acetabular prosthesis of claim 12, wherein the metallic outer reinforcement layer has a thickness of approximately 0.5 millimeters.

15. The modular acetabular prosthesis of claim 12, wherein the metallic outer reinforcement layer comprises a concave inner wall having a porous surface to which the polymeric inner bearing layer is molded.

16. The modular acetabular prosthesis of claim 15, wherein the metallic outer reinforcement layer is 3D printed.

17. The modular acetabular prosthesis of claim 15, wherein the porous surface is a coating on the metallic material.

18. The modular acetabular prosthesis of claim 12, wherein the metallic outer reinforcement layer is constructed of at least one of titanium, cobalt chromium, stainless steel, or medium grade high strength steel.

19. A method for using a modular acetabular prosthesis in a hip arthroplasty surgical procedure comprising:
    implanting an acetabular shell component into a surgically-prepared acetabulum of a patient; and
    securing, into the acetabular shell component, a liner component that includes a semi-hemispherical polymeric inner bearing layer that is at least partially encased in a semi-hemispherical metallic outer reinforcement layer, wherein the semi-hemispherical polymeric inner bearing layer includes a cylindrical rim and a dome extending away from the cylindrical rim, wherein the cylindrical rim includes an inner wall and an outer wall parallel with the inner wall and wherein the cylindrical rim extends past and wraps onto a rim of the semi-hemispherical metallic outer reinforcement layer.

20. The method of claim 19, further comprising positioning a head of a femoral prosthesis to bear on the polymeric inner bearing layer of the liner component.

* * * * *